US005968556A

United States Patent [19]
Atala et al.

[11] Patent Number: 5,968,556
[45] Date of Patent: *Oct. 19, 1999

[54] INJECTABLE NON-IMMUNOGENIC CARTILAGE AND BONE PREPARATION

[75] Inventors: Anthony Atala, Weston; Samy Ashkar, Boston, both of Mass.

[73] Assignee: Children's Medical Center Corp., Boston, Mass.

[ * ] Notice: This patent is subject to a terminal disclaimer.

[21] Appl. No.: 08/630,734

[22] Filed: Apr. 2, 1996

Related U.S. Application Data

[63] Continuation of application No. 08/286,273, Aug. 5, 1994, Pat. No. 5,516,532.

[51] Int. Cl.⁶ .................................................. A61K 35/32
[52] U.S. Cl. ........................ 424/548; 424/549; 424/423; 424/426; 623/11; 623/16
[58] Field of Search ..................................... 424/548, 549, 424/423, 426; 623/11, 16

[56] References Cited

U.S. PATENT DOCUMENTS

| | | | |
|---|---|---|---|
| 4,172,128 | 10/1979 | Thiele et al. | 424/95 |
| 5,092,887 | 3/1992 | Gendler | 623/13 |
| 5,112,354 | 5/1992 | Sires | 623/16 |
| 5,328,695 | 7/1994 | Lucas et al. | 424/426 |
| 5,336,263 | 8/1994 | Ersek et al. | 623/11 |
| 5,516,532 | 5/1996 | Atala et al. | 424/548 |

FOREIGN PATENT DOCUMENTS

| | | | |
|---|---|---|---|
| 0 082 621 | 6/1983 | European Pat. Off. | A61F 1/00 |
| 0 495 284 A1 | 7/1992 | European Pat. Off. | A61L 27/00 |
| 2 175 506 | 12/1986 | United Kingdom | A61F 1/00 |
| 90/10018 | 9/1990 | WIPO | C07K 15/00 |
| 94/21299 | 9/1994 | WIPO | A61K 47/38 |

OTHER PUBLICATIONS

Atala, et al., "Laparoscopic Correction of Vesicoureteral Reflux", *The Journal of Urology*, vol. 150, pp. 748–751 (1993).
Atala, et al., "Endoscopic Treatment of Vesicoureteral Reflux With A Self–Detachable Balloon System", *The Journal of Urology*, vol. 148, pp. 724–728 (1992).
Atala, et al. "Injectable Alginate Seeded With Chondrocytes As A Potential Treatment for Vesicoureteral Reflux", *The Journal of Urology*, vol. 150, pp. 745–747 (1993).
Atala, et al., "Sonography With Sonicated Albumin in The Detection Of Vesicoureteral Reflux",, *The Journal of Urology*, vol. 150, pp. 756–758 (1993).
Claes, et al., "Pulmonary Migration Following Periurethral Polytetrafluoroethylene Injection For Urinary Incontinence", *The Journal of Urology*, vol. 142, pp. 821–822 (1989).
Geiss, et al., "Multicenter Survey of Endoscopic Treatment of Vesicoureteral Reflux in Children", *Eur. Urol.*, vol. 17, pp. 328–329 (1990).
Ferro, et al., "Periurethral Granuloma: Unusual Complication of Teflon Periurethral Injection", *Urology*, vol. 31, pp. 422–423 (1988).

Klagsbrun, "Large–Scale Preparation of Chondrocytes", *Methods in Enzymology*, vol. 58, pp. 560–564 (1979).
Leonard, et al., "Endoscopic Injection of Glutaraldehyde Cross–Linked Bovine Dermal Collagen For Correction of Vesicoureteral Reflux", *The Journal of Urology*, vol. 145, pp. 115–119 (1991).
Malizia, et al., "Migration and Granulomatous Reaction After Periurethral Injection of Polytef (Teflon)", *JAMA*, vol. 251, pp. 3277–3282 (1984).
Matousche, "Medical versus Surgical Treatment of Primary Vesicoureteral Reflux: A Prospective International Reflux Study in Children", *The Journal of Urology*, vol. 125, pp. 277–283 (1981).
Mittleman, et al., "Pulmonary Teflon Granulomas Following Periurethral Teflon Injection for Urinary Incontinence", *Arch. Pathol Lab Med*, vol. 107, pp. 611–612 (1983).
O'Donnell, et al., "Treatment of Vesicoureteric Reflux by Endoscopic Injection of Teflon", *British Medical Journal*, vol. 289, pp. 7–9 (1984).
Vorstman, et al., "Polytetrafluoroethylene Injection for Urinary Incontinence in Children", *The Journal of Urology*, vol. 133, pp. 248–250 (1985).
Walker, et al., "Injectable Bioglass as a Potential Substitute for Injectable Polytetrafluoroethylene", *The Journal of Urology*, vol. 148, pp. 645–647 (1992).
Atala, "Extravesical Reimplantation (Detrusorrhaphy) Revisited", *Dialogues in Pediatric Urology*, vol. 16, pp. 1–8 (1993).
Atala, et al., "Management of Primary Vesicoureteral Reflux", *Infections in Urology*, Mar./Apr. 1990, pp. 39–43.
Buckley, et al., "Endoscopic correction of Vesicoureteric Reflux with Injectable Silicone Microparticles", *Journal of Urology*, (Abstract), Abstract No. 573 (1993).
Henly, et al., "Particulate Silicone for Use in Periurethral Injections: A Study of Local Tissue Effects and a Search for Migration", *Journal of Urology* (Abstract), Abstract No. 654 (1992).
Mulliken et al., "Use of Demineralized Allogeneic Bone Implants For The Correction of Maxillocraniofacial Deformities", Ann Surg, Sep. 1981; 194 (3): 366–72 (Abstract only).
Rames, et al., "Migration of polytef paste to the lung and brain following intravesical injection for the correction of reflux", *Pediatric Surgery International*, vol. 6, No. 1991.

*Primary Examiner*—Jean C. Witz
*Attorney, Agent, or Firm*—Lahive & Cockfield LLP

[57] ABSTRACT

Ground bone or cartilage particles are demineralized by extraction with a low ionic strength buffer such as 20 mM HEPES containing a chelating agent and protease inhibitors, then extracted with an acidic solution such as 0.3 M citric acid, pH 4.0, containing protease inhibitors. The extracted material generally contains less than 2% by weight phosphate and less than 100 mM calcium. The phosphate content can be further reduced by treatment of the matrix with acid phosphatase, which removes residual organic phosphate. The material is useful in a method of treatment of vesicouretal reflux and other disorders where a bulking agent is effective is correcting the defect.

26 Claims, 1 Drawing Sheet

INJECTABLE NON-IMMUNOGENIC CARTILAGE AND BONE PREPARATION

This application is a continuation of U.S. application Ser. No. 08/286,273, filed Aug. 5, 1994, now U.S. Pat. No. 5,516,532.

BACKGROUND OF THE INVENTION

The present invention is generally in the area of medical treatments, and specifically relates to an method for making a non-immunogenic cartilage and bone preparation and use thereof as a bulking agent.

Vesicouretal reflux is a condition wherein there is an abnormal development of the ureteral bud as it enters the bladder during embryologic development. The shortened course of the ureter through the bladder musculature decreases the ureteral resistance and allows for urine to reflux from the bladder reservoir back up into the ureter and into the kidney. With this condition, bacteria which may occasionally be present in the bladder through retrograde urethral transport, can reach the kidneys and cause recurrent pyelonephritis. In addition, the constant back pressure of the urine into the calyces and renal pyramids results in mechanical damage to the renal parenchyma. If untreated, urinary vesicoureteral reflux can cause loss of renal parenchyma, and in some instances, renal failure, as reviewed by Atala and Casale, *Infections in Urology* 39–43 (March/April 1990). In 1960, 70% of the patients with renal failure were described as having vesicoureteral reflux as the primary etiology. With the advent of new diagnostic and treatment modalities, patients with vesicoureteral reflux now account for less than 1% of the renal failure population.

The initial management of vesicoureteral reflux usually consists of suppressive antibiotics in anticipation of spontaneous resolution, as described by Atala, et al., "Sonography with sonicated albumin in the detection of vesicoureteral reflux" *J. Urol.* 150:756–758 (1993). Depending on the severity of reflux, 20 to 60 percent of patients may ultimately undergo surgical treatment, as reported by Klagsbrun, M. "Large scale preparation of chondrocytes" Methods in Enzymology 58:560 (1979); O'Donnell and Puri, "Treatment of vesicoureteic reflux by endoscopic injection of Teflon" *Brit. Med. J.* 289: 7 (1984). Although open surgical procedures for the correction of reflux have excellent results in the hands of experienced surgeons, it is associated with a well recognized morbidity, including pain and immobilization of a lower abdominal incision, bladder spasms, hematuria, and post-operative voiding frequency in some children.

The endoscopic treatment of vesicoureteral reflux was first introduced in 1981 when Polytetrafluoroethylene (Teflon) was injected in the subureteral region of a patient, as reported by Matouschek, E.: Die Behandlung des vesikorenalen Refluxes durch transueterale Einspritzung von polytetrafluoroethylenepaste. *Urologe,* 20:263 (1981). In an effort to avoid open surgical intervention, widespread interest in the endoscopic treatment of reflux was initiated by O'Donnell and Puri's clinical experience with Polytetrafluoroethylene paste in 1984, (Atala and Casale "Management of primary vesicoureteral reflux" *Infections in Urol.* 2:39 (1990)). Soon thereafter, a controversy regarding the use of polytetrafluoroethylene paste ensued. Particle migration to distant organs raised concerns regarding the use of polytetrafluoroethylene paste, as reported by Malizia, et al., "Migration and granulomatous reaction after periurethral injection of polyef (polytetrafluoroethylene)" *JAMA,* 251:3277 (1984); Claes, et al., "Pulmonary migration following periurethral polytetrafluoroethylene injection for urinary incontinence" *J. Urol.* 142:821 (1989); Vorstman, et al., "Polytetraflouroethylene injection for urinary incontinence in children" *J. Urol.* 133:248 (1985); Mittleman, et al., "Pulmonary polytetrafluoroethylene granulomas following periurethral polytetrafluoroethylene injection for urinary incontinence" *Arch. Path. Lab. Med.* 107:611 (1983); Ferro, et al., "Periurethral granuloma: Unusual complications of Teflon periurethral injection" *Urology* 31:422 (1988); Rames, et al., "Migration of polystef paste to the lung and brain following intravesical injection for the correction of reflux" *Ped. Surg. Int.* 6:239 (1991).

Bovine dermal collagen preparations have been used to treat reflux endoscopically, as reported by Leonard, et al., "Endoscopic injection of glutaraldehyde cross-linked bovine dermal collagen for correction of vesicoureteral reflux" *J. Urol.* 145:115 (1991). However, only 58.5% of the patients were cured at one year follow-up. The collagen implant volume decreases with time, which results in a high percentage of recurrence of reflux. The high rate of retreatment necessary due to implant volume loss has limited the usefulness of collagen, as discussed in "Medical versus surgical treatment of primary vesicoureteral reflux: a prospective international reflux study in children" Report of the International Reflux Study Committee. *J. Urol,* 125:277 (1981). The ideal implant material should be non-migratory, non-antigenic, able to be delivered endoscopically, and should conserve its volume.

A paste consisting of textured microparticles of silicone, suspended in a hydrogel, has been injected subureterally to correct reflux with an initial success rate of 91%, as reported by Buckley, et al., "Endoscopic correction of vesicoureteric reflux with injectable microparticulate silicone" Abstract 573 presented at 87th Annual Meeting, AUA, May 10–14, 1993, Washington DC. Although problems have been encountered with the silicone gel-filled prostheses which have the potential to rupture or leak, the solid silicone prostheses have been mostly problem-free. Recently however, concerns have also been raised regarding the non-gel-filled prostheses. Barrett et al. "Particle shedding and migration from silicone genitourinary prosthetic devices" *J. Urol.* 146:319–322 (1991), showed silicone particles from 18 of 25 urologic periprosthetic specimens, and in all lymph nodes examined. Foreign body granulomas were identified in 29 specimens. Lymphadenopathy and lymphadenitis have occurred after silicone prosthesis implantation (Paplanus and Payne "Axillary lymphadenopathy 17 years after digital silicone implants: study with x-ray microanalysis" *J. Hand. Surg.* 13:399 (1988); Endo, et al., "Silicone and rheumatic diseases" *Sem. Arth. Rheum.* 17:112 (1987)). Silicone particles have been found in the enlarged nodes of patients with malignant lymphoma (Digby "Malignant lymphoma with intranodal silicone rubber particles following metacarpophalangeal joint replacements" *Hand* 14:326 (1982); Benjamin, et al., "Silicone lympadenopathy: a report of two cases, one with concomitant malignant lymphoma" *Diaan. Histopath.* 5:133 (1982)). The autoimmune disorder human adjuvant disease, is associated with silicone implantation (Sergott, et al., "Human adjuvant disease possible autoimmune disease after silicone implantation: a review of the literature, case studies, and speculation for the future" *Plast. Reconstr. Surg.* 78:104 (1986)). Long-term longitudinal studies of patients with silicone prostheses are needed to define the associated risk.

Other materials for the endoscopic treatment of reflux, including a detachable balloon system (Atala et al., "Endoscopic treatment of vesicoureteral reflux with a self-detachable balloon system", *J. Urol.* 148:724 (1992)) and Bioglass (Walker, et al., "Injectable bioglass as a potential substitute for injectable polytetrafluoroethylene" *J. Urol.* 148:645 (1992)) are currently under investigation and have not been used in a clinical setting.

Laparoscopic correction of reflux has been attempted in both an animal model (Atala, et al., "Laparoscopic correction of vesicouretal reflux" *J. Urol.* 150:748–751 (1993)) and humans (Atala, "Laparoscopic treatment of vesicoureteral reflux" *Dial Ped Urol* 14:212 (1993)) and is technically feasible. However, at least two surgeons with laparoscopic expertise are needed, the length of the procedure is longer than with open surgery, and the cost is higher due to both increased operative time and the expense of the disposable laparoscopic equipment.

The advantages of the endoscopic treatment for reflux cannot be overlooked. The method is simple, can be completed in less than 15 minutes as an outpatient procedure, has a low morbidity and a success rate of more than 85 percent, as reported by Giss, et al., "Multicenter survey of endoscopic treatment of vesicoureteral reflux in children" *Eur. Urol.* 17:328 (1990). The ideal substance for the endoscopic treatment of reflux should be injectable, non-antigenic, non-migratory, volume stable, and safe for human use.

Urinary incontinence.

Urinary Incontinence is the most common and the most intractable of all GU maladies. Urinary incontinence, or the inability to retain urine and not void urine involuntarily, is dependent on the interaction of two sets of muscles. One is the detrusor muscle, a complex of longitudinal fibers forming the external muscular coating of the bladder. The detrusor is activated by parasympathetic nerves. The second muscle is the smooth/striated muscle of the bladder sphincter. The act of voiding requires the sphincter muscle be voluntarily relaxed at the same time that the detrusor muscle of the bladder contracts. As a person ages, his ability to voluntarily control the sphincter muscle is lost in the same way that general muscle tone deteriorates with age. This can also occur when a radical event such as paraplegia "disconnects" the parasympathetic nervous system causing a loss of sphincter control. In different patients, urinary incontinence exhibits different levels of severity and is classified accordingly.

The most common incontinence, particular in the elderly, is urge incontinence. This type of incontinence is characterized by an extremely brief warning following by immediate urination. This type of incontinence is caused by a hyperactive detrusor and is usually treated with "toilet training" or medication. Reflex incontinence, on the other hand, exhibits no warning and is usually the result of an impairment of the parasympathetic nerve system such as a spinal cord injury.

Stress incontinence is most common in elderly women but can be found in women of any age. It is also commonly seen in pregnant women. This type of incontinence accounts for over half of the total number of cases. It is also found in men but at a lower incidence. Stress incontinence is characterized by urine leaking under conditions of stress such as sneezing, laughing or physical effort. There are five recognized categories of severity of stress incontinence, designated as types as 0, 1, 2a, 2b, and 3. Type 3 is the most severe and requires a diagnosis of intrinsic Sphincter Deficiency or ISD (Contemporary Urology, March 1993). There are many popular treatments including weight loss, exercise, medication and in more extreme cases, surgical intervention. The two most common surgical procedures involve either elevating the bladder neck to counteract leakage or constructing a lining from the patient's own body tissue or a prosthetic material such as PTFE to put pressure on the urethra. Another option is to use prosthetic devices such as artificial sphincters to external devices such as intravaginal balloons or penile clamps. For treatment of type 3 stress incontinence, there has been a recent trend toward injection of Teflon™ or collagen paste around the sphincter muscle in order to "beef up" the area and improve muscle tone. None of the above methods of treatment, however, are very effective for periods in excess of a year.

Overflow incontinence is caused by anatomical obstructions in the bladder or underactive detrustors. It is characterized by a distended bladder which leads to frequent urine leakage. This type of incontinence is treated acutely by catheterization and long-term by drug therapy. Enuresis or bed-wetting is a problem in pediatrics and is controlled by various alarming devices and pads with sensors. Enuresis is not considered a serious problem unless it lasts beyond the age of four or five. Finally, there is true functional incontinence which occurs in patients with chronic impairment either of mobility or mental function. Such patients are usually treated by the use of diapers, incontinence pads or continuous catheterization (BBI, 1985 Report 7062).

It is therefore an object of the present invention to provide a method and material for treating vesicouretal reflux which results in a natural and permanent cure to the defect.

It is a further object of the present invention to provide a method and material for treating vesicouretal reflux which is quick, simple, safe, and relatively non-invasive.

It is another object of the present invention to provide a bulking material which is non-biodegradable, biocompatible, non-migratory, and can be injected.

SUMMARY OF THE INVENTION

A method of treatment of vesicouretal reflux and incontinence is described wherein a non-immunogenic demineralized bone and cartilage suspension is prepared that can be mixed with polymeric carriers and/or other pharmaceutically acceptable materials for injection. Examples of suitable polymeric carriers include polyvinylpyrrolidone (PVP), hyaluronic acid, fibrin, glue, saline, alginate, and other polymers forming a hydrogel. The resulting suspension is injectable and can be used for correction of a variety of tissue defects and incontinence. For example, it can be injected into the area where reflux is occurring, in an amount effective to provide the required control over the passage of urine.

In the preferred embodiment, ground bone or cartilage particles are demineralized by extraction with a low ionic strength buffer such as 20 mM HEPES containing a chelating agent and protease inhibitors, then extracted with an acidic solution such as 0.3 M citric acid, pH 4.0, containing protease inhibitors. The extracted material generally contains less than 2% by weight phosphate and less than 100 mM calcium. The phosphate content can be further reduced by treatment of the matrix with acid phosphatase, which removes residual organic phosphate.

DETAILED DESCRIPTION OF THE INVENTION

Source of Cartilage and Bone

Figure 1:
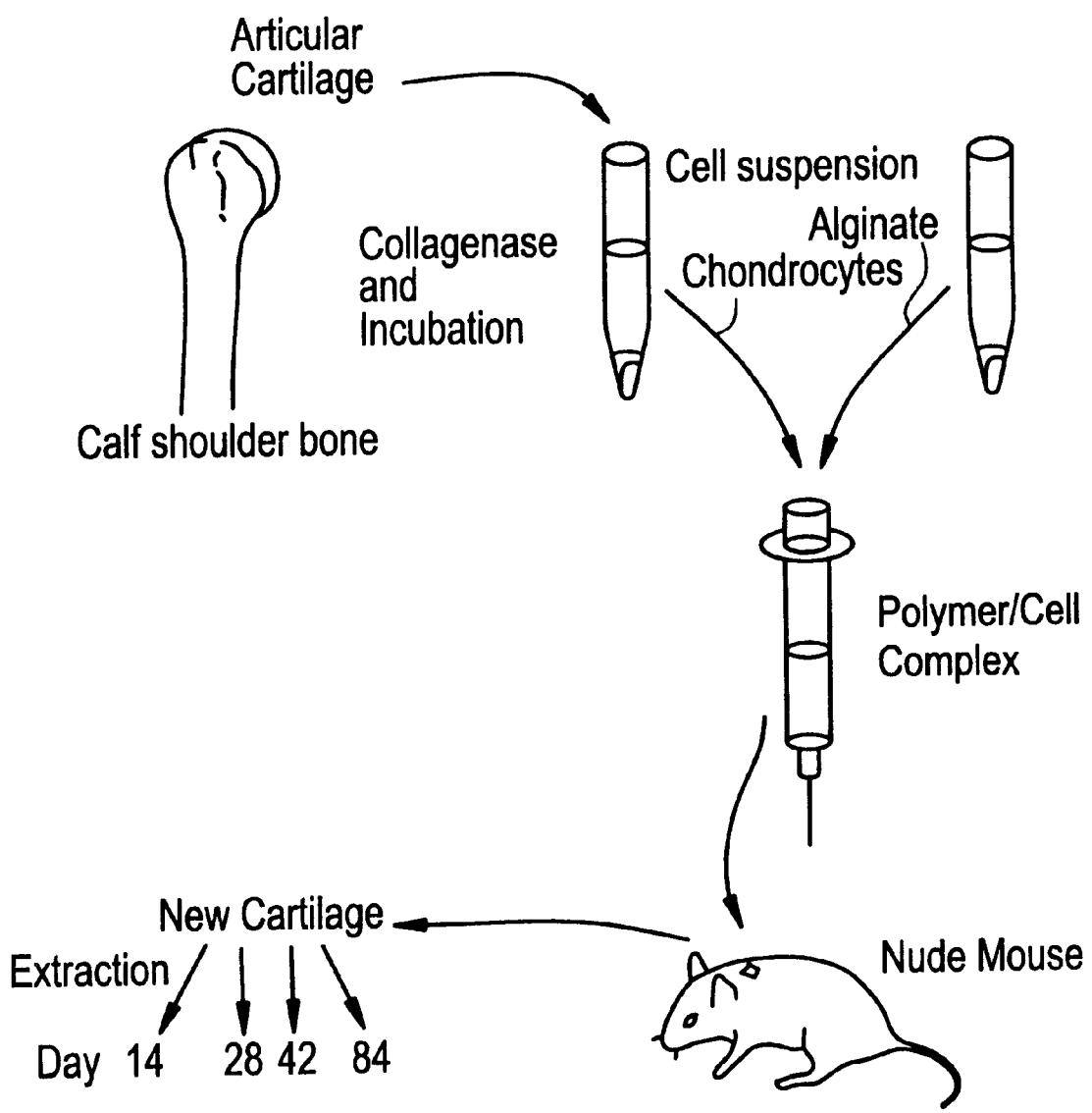
FIG. 1 is a schematic of the preparation of and injection of a non-immunogenic cartilage and bone suspension into a region for control of vesicouretal reflux or incontinence.

In the preferred embodiment, cartilage and/or bone is obtained from the diaphyses of the metatarsal bones or articular cartilage. Hyaline cartilage is the most common type of cartilage. Between the diaphysis and the epiphysis of growing long bones, the epiphyseal plate is composed of hyaline cartilage. In adults, hyaline cartilage is located in the articular surfaces of the movable joints.

Forty percent of the dry weight of hyaline cartilage consists of collagen embedded in an amorphous intercellular substance.

Bone is a very dense, specialized form of connective tissue. It is a mixture of type I collagen fibrils and solid inorganic matter. Inorganic matter represents about 50% of the dry weight of bones. Calcium and phosphorus are especially abundant, although bicarbonate, citrate, magnesium, potassium, and sodium are also found. The calcium and phosphorus form hydroxyapatite crystals.

The method described herein removes most of the inorganic material from the organic material, to leave an organic matrix useful as a bulking agent to correct tissue defects.

Preparation of Cartilage and Bone

The cartilage and/or bone is cleaned, ground in a liquid nitrogen cooled mill to a particle size ranging from 80 to 200 microns, and washed four times with ice cold (0 to 4° C.) phosphate buffered saline (PBS). 80 gm of bone or cartilage particles are demineralized with 500 ml of prechilled (0 to 4° C.) 20 mM HEPES buffer, within a pH range of 6 to 8, preferably 7.4, total ionic strength 5.02, containing a calcium chelating agent such as 0.5 M ethylenediaminetetraacetic acid (EDTA) and protease inhibitors, for example, 1 mM phenylmethylsulfonyl fluoride, 5 mM benzamidine, 0.1 mM epsilon-amino caproic acid, 0.1 β-hydroxy mercuribenzoate, 0.1 mM pyrophosphate, 1 mM sodium fluoride, 1 mM sodium orthovanadate, 10 mM levamisole, and 1 µg/ml pepstatin A (all available from Sigma Chemical Co, St. Louis, Mo.), for one to seven days, preferably for two days, at a temperature of between 0 and 6° C., preferably at 2° C. The bone particles are then collected by centrifugation, for example in a GSA rotor at 4000×g for 30 minutes. The pellet is then reextracted in the HEPES buffer and again collected by centrifugation. The centrifuged solids are then extracted with 1 liter of 0.3 M citric acid pH 4.0 containing protease inhibitors, for one week at 2° C. The solids are again harvested by centrifugation as described above, and washed three times with 500 ml of 20 mM HEPES pH 7.4 containing 1 M NaCl followed by three washes with 250 ml of 20 mM HEPES pH 7.4. The wet matrix is dried under vacuum and stored at −20° C.

The resulting material is a demineralized particulate organic matrix having a phosphate content of less than 2% (by weight) and a calcium concentration of less than 1 mg calcium per gram of matrix, preferably less than 0.5 mg calcium per gram of matrix. Calcium is determined by atomic absorption spectroscopy. The phosphate content of the matrix can be further reduced by treating the matrix with acid phosphatase (0.1 U/mg matrix) in 0.05 M glycine buffer, pH 4.0 for 6 h at 4° C.; or bacterial alkaline phosphase at pH 9.0, or 3 N NaOH at 50° C. for 30 minutes. This treatment removes any residual organic phosphates and reduces the total phosphate content to less than 1%, preferably to less than 0.5%, or less than 20 mg of phosphate per gram of matrix, preferably less than 10 mg of phosphate per gram of matrix. The major remaining constituent of the matrix is collagen type I (type II for cartilage). Other components of the matrix are collagen type IX, proteoglycans, and trace amounts of osteopontin, osteocalcin, osteonectin and bone sialoprotein. This process renders the remaining substrate substantially non-immunogenic.

Polymer Suspensions

A suitable material for a suspension of the particles is biocompatible to preclude migration and immunological complications. It should most preferably also be resorbable over a period of three to six months, allowing for a completely natural tissue replacement. Different polymers can be used to create a matrix suspension which is injected into the patient. In the preferred embodiment, calcium alginate or biocompatible polymers that can form ionic hydrogels which are malleable are used to suspend the matrix. In the preferred embodiment, the hydrogel is produced by cross-linking the anionic salt of alginic acid, a carbohydrate polymer isolated from seaweed, with calcium cations, whose strength increases with either increasing concentrations of calcium ions or alginate. The alginate solution is mixed with the matrix to be implanted to form an alginate suspension. The suspension is then injected directly into a patient prior to hardening of the suspension. The suspension subsequently hardens over a short period of time due to the presence in vivo of physiological concentrations of calcium ions to form a hydrogel.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates, which are crosslinked ionically, or block copolymers such as Pluronics™ or Tetronics™, polyethylene oxide-polypropylene glycol block copolymers which are crosslinked by temperature or pH, respectively, or light or radiation.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure (1):

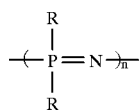

where n is an integer.

The polyphosphazenes suitable for crosslinking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegrable, as used herein, means a polymer that dissolves or degrades within a period that is acceptable in the desired application (usually in vivo therapy), once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824–830 (1977).

Methods for synthesis and the analysis of various types of polyphosphazenes are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, et al., *Biomaterials,* 19, 500 (1988); Allcock,¯ et al., *Macromolecules* 21, 1980 (1988); Allcock, et al., *Inorg. Chem.* 21(2), 515–521 (1982); Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al.; and Grolleman, et al., *J. Controlled Release* 3, 143 (1986), the teachings of which are specifically incorporated herein by reference.

Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly (acrylic acid) and polyvinylpyrrolidone, are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$—\/\/\/—$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

Other types of polymeric carriers that can be utilized are naturally occurring polymers such as hyaluronic acid and fibrin glue.

Matrix Suspensions

The matrix material can be suspended in an aqueous solution such as phosphate buffered saline or mixed with a polymeric material of the type described above. In the latter case, the matrix and polymer is preferably dissolved in water, saline, buffer or polymeric solution to form a suspension.

Injection of Matrix Suspension

Vesicoureteral reflux is one of the most common congenital defects in children, affecting approximately 1% of the population. Although all patients do not require surgical treatment, it is still one of the most common procedure performed in children. Over 600 ureteral reimplants are performed yearly at Children's Hospital in Boston, Mass. This translates to an approximately saving of 3600 inpatient hospital days per year at this institution alone, if the endoscopic treatment described herein is used instead of open surgery.

As described herein, an injectable biodegradable demineralized organic matrix derived from cartilage and/or bone is useful in the treatment of reflux. In the preferred embodiment, the matrix material is mixed with a polymeric material such as alginate, and the matrix-polymer suspension is injected endoscopically in the sub-ureteral region to correct reflux. In one embodiment, the time to solidification of the polymeric-matrix suspension may be manipulated by varying the concentration of calcium as well as the temperature at which the chondrocytes are added to the alginate. The use of autologous cartilage or bone precludes an immunologic reaction. Solidification of the alginate impedes its migration until after it is degraded.

The suspension can be injected through a cystoscopic needle, having direct visual access with a cystoscope to the area of interest, such as for the treatment of vesico-ureteral reflux or urinary incontinence. In addition to the use of the chondrocyte-polymer suspension for the treatment of reflux and incontinence, the suspension can also be applied to reconstructive surgery, as well as its application anywhere in the human body where a biocompatible permanent injectable material is necessary, such as for repair of soft or hard tissue defects. The suspension can be injected endoscopically, for example through a laryngoscope for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscopic or thoracoscope to any intraperitoneal or extraperitoneal or thoracic organ. For example, the suspension could be injected in the region of the gastro-esophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

The system of injectable non-immunogenic cartilage and bone preparation may also be applicable for the treatment of other medical conditions, such as dysphonia.

The present invention will be further understood by reference to the following non-limiting example. The example demonstrates that the matrix-polymer suspension is injectable, non-migratory, and appears to conserve its volume, and is useful in the endoscopic treatment of vesicoureteral reflux.

Example 1: Non-immunogenic Demineralized Bone as a Potential Treatment for Vesicouretal Reflux Diaphyses of bovine metatarsal bones were cleaned, ground in a liquid nitrogen cooled mill, and washed with ice cold phosphate buffered saline containing protease inhibitors. The bone particles were demineralized and collected by centrifugation. The matrix was then extracted with 0.3 M citric acid at 2° C. The wet matrix was dried under vacuum and stored at 20° C. until used. The process renders the matrix nonimmunogenic.

The demineralized substrate was mixed with polyvinylpyrrolidone (PVP), a hydrophilic carrier which is a biologically compatible substance. Thirty nude mice were injected with a 500 microliter solution. Each mouse was injected at one site with a solution of demineralized bone substrate with PVP and at a different site with a control (60 injection sites) of PVP alone. Animals were sacrificed at two, four, six,-eight and twenty weeks after implantation.

Histologic examination of the injection areas demonstrated a bead of demineralized bone substrate. Examination of the injection sites over increasing periods of time showed that the size of the substrate complex appeared to be uniform and stable. The control sites injected with PVP alone showed full reabsorption with no untoward effects. Histologic analysis of distant organs showed no evidence of bone matrix migration or granuloma formation.

Modifications and variations of the present invention will be obvious to those skilled in the art from the foregoing detailed description. Such modifications and variations are intended to come within the scope of the appended claims.

We claim:

1. A method for correcting a tissue defect comprising administering to a patient in need of treatment thereof a demineralized organic matrix suspension, wherein the organic matrix is prepared by leaching of cartilage or bone to produce an organic material containing less than 2% by weight of phosphate and less than 100 mM calcium.

2. The method of claim 1 wherein the matrix is prepared by grinding bone and/or cartilage to form particles having a diameter of between approximately 80 and 200 microns and leaching out calcium and other divalent ions with a buffered aqueous chelating solution and 1 M salt solution.

3. The method of claim 2 wherein the matrix is prepared by treatment with acid phosphatase to remove phosphate remaining after leaching with aqueous chelating and salt solutions.

4. The method of claim 1 wherein the matrix is suspended in a pharmaceutically acceptable carrier.

5. The method of claim 4 wherein the carrier is selected from the group consisting of buffered aqueous solutions and biocompatible, biodegradable polymer solutions.

6. The method of claim 5 wherein the polymer is crosslinked in vivo to form a hydrogel encapsulating the matrix.

7. The method of claim 5 wherein the polymer is a polysaccharide, a polyphosphazene, a polyacrylate, a polyethyleneoxide-polypropylene glycol block copolymer, polyvinylpyrrolidone, a fibrin glue, or a hyaluronic acid.

8. The method of claim 1 wherein the material is administered to correct vesicoureteral reflux.

9. The method of claim 1 wherein the material is administered to correct incontinence.

10. The method of claim 1 wherein the material is to block tubes and sterilize an individual.

11. A method for isolating an organic matrix from cartilage or bone comprising
    obtaining a material from the group consisting of growing bone and cartilage,
    leaching the material with an aqueous chelating solution at a temperature less than 6° to 15° C. to yield a de-calcified solid,
    extracting the leached solid with an acidic solution containing protease inhibitors at a temperature less than 6° C. to 15° C., and
    further extracting the extracted leached solid with a salt solution at a temperature of less than 6° C. to 15° C. to yield a demineralized material having a total phosphate content of less than 2% by weight and less than 100 mM phosphate.

12. The method of claim 11 further comprising
treating the demineralized material with acid phosphatase to decrease the phosphate content of the resulting material to less than 1% by weight.

13. The method of claim 11 wherein the chelating agent is an aqueous solution of EDTA.

14. The method of claim 11 wherein the salt solution is a sodium chloride solution.

15. The method of claim 11 wherein the starting material is cartilage.

16. The method of claim 11 wherein the starting material is bone.

17. A demineralized organic matrix prepared by the method comprising
obtaining a material from the group consisting of growing bone and cartilage, leaching the material with an aqueous chelating solution at a temperature less than 6° C. to 15° C. to yield a de-calcified solid,
extracting the leached solid with an acidic solution containing protease inhibitors at a temperature less than 6° C. to 15° C., and
further extracting the extracted leached solid with a salt solution at a temperature of less than 6° C. to 15° C. to yield a demineralized material having a total phosphate content of less than 2% by weight and less than 100 mM calcium.

18. The material of claim 17 wherein the method further comprises
treating the demineralized material acid phosphatase to decrease the phosphate content of the resulting material to less than 1% by weight.

19. The material of claim 17 wherein the starting material is cartilage.

20. The material of claim 17 wherein the starting material is bone.

21. The method of claim 7 wherein the polymer is crosslinked by temperature.

22. The method of claim 7 wherein the polymer is crosslinked by pH.

23. The method of claim 7 wherein the polymer is crosslinked ionically.

24. The method of claim 7 wherein the polymer is crosslinked via covalent bonds.

25. The method of claim 7 wherein the polymer is crosslinked by light.

26. The method of claim 7 wherein the polymer is crosslinked by radiation.

* * * * *